United States Patent
Hata et al.

(10) Patent No.: US 10,072,861 B2
(45) Date of Patent: Sep. 11, 2018

(54) CLEAN WORK DEVICE

(71) Applicant: JAPAN TISSUE ENGINEERING CO, LTD., Gamagori-shi, Aichi (JP)

(72) Inventors: Ken-ichiro Hata, Kariya (JP); Makoto Sugiura, Gifu (JP)

(73) Assignee: JAPAN TISSUE ENGINEERING CO., LTD., Gamagori-shi (JP)

(*) Notice: Subject to any disclaimer, the term of this patent is extended or adjusted under 35 U.S.C. 154(b) by 258 days.

(21) Appl. No.: 14/914,796

(22) PCT Filed: Oct. 23, 2014

(86) PCT No.: PCT/JP2014/078213
§ 371 (c)(1),
(2) Date: Feb. 26, 2016

(87) PCT Pub. No.: WO2015/060383
PCT Pub. Date: Apr. 30, 2015

(65) Prior Publication Data
US 2016/0298867 A1  Oct. 13, 2016

(30) Foreign Application Priority Data
Oct. 25, 2013  (JP) .................................. 2013-222187

(51) Int. Cl.
*B65G 45/00* (2006.01)
*F24F 7/08* (2006.01)
(Continued)

(52) U.S. Cl.
CPC .................. *F24F 7/08* (2013.01); *B01L 1/00* (2013.01); *B01L 1/04* (2013.01); *B01L 9/06* (2013.01);
(Continued)

(58) Field of Classification Search
CPC ... F24F 7/08; F24F 3/1607; B01L 1/00; B01L 1/04; B01L 9/06; B01L 9/543; C12M 39/00
See application file for complete search history.

(56) References Cited

U.S. PATENT DOCUMENTS 2,155,932 A * 4/1939 Davis ...................... C03C 15/00
118/326
3,106,927 A * 10/1963 Madwed .............. B65G 49/049
134/115 R
(Continued)

FOREIGN PATENT DOCUMENTS

EP  0309351 A1  3/1989
JP  H01-85317 U  6/1989
(Continued)

OTHER PUBLICATIONS

Apr. 26, 2016 International Preliminary Report on Patentability issued in International Patent Application No. PCT/JP2014/078213.
(Continued)

*Primary Examiner* — William R Harp
(74) *Attorney, Agent, or Firm* — Oliff PLC (57) ABSTRACT

A work area is disposed in a conveyance path for cells and has an inlet and an outlet, with a downflow air curtain provided at least at the inlet and the outlet. A conveyor repeatedly performs an operation that moves a placement surface having a culture vessel thereon from the inlet side into the area, moves the placement surface from the outlet side to the outside of the area, and, subsequently, moves back the placement surface to the inlet side. The cleaning device cleans the placement surface during the period from when the conveyor in the work area moves the placement surface to the outside of the area until the conveyor moves back the placement surface to the inlet side of the area.

10 Claims, 5 Drawing Sheets

(51) Int. Cl.
- *F24F 3/16* (2006.01)
- *B01L 9/06* (2006.01)
- *C12M 1/00* (2006.01)
- *B01L 1/00* (2006.01)
- *B01L 9/00* (2006.01)
- *F24F 9/00* (2006.01)
- *B01L 1/04* (2006.01)

(52) U.S. Cl.
CPC .............. *B01L 9/543* (2013.01); *C12M 39/00* (2013.01); *F24F 3/1607* (2013.01); *F24F 9/00* (2013.01); *B01L 2200/141* (2013.01)

(56) References Cited

U.S. PATENT DOCUMENTS

| | | | | |
|---|---|---|---|---|
| 3,352,627 | A * | 11/1967 | Indreland | D06F 58/12 34/506 |
| 4,321,031 | A * | 3/1982 | Woodgate | B23K 1/015 219/388 |
| 5,425,793 | A * | 6/1995 | Mori | B01D 46/0013 454/187 |
| 6,683,312 | B2 * | 1/2004 | Yun | B08B 7/0057 250/455.11 |
| 7,234,586 | B1 * | 6/2007 | Newman | A23G 9/30 198/495 |
| 8,322,518 | B2 | 12/2012 | Ball | |
| 2011/0253507 | A1 | 10/2011 | Ball | |
| 2012/0190180 | A1 * | 7/2012 | LoBue | H01L 21/02554 438/486 |

FOREIGN PATENT DOCUMENTS

| | | |
|---|---|---|
| JP | H10-302017 A | 11/1998 |
| JP | 2000-085963 A | 3/2000 |
| JP | 2003-083579 A | 3/2003 |
| JP | 2005-201488 A | 7/2005 |
| JP | 2006-162090 A | 6/2006 |
| JP | 2006-292201 A | 10/2006 |
| JP | 2008-275266 A | 11/2008 |
| JP | 2013-523567 A | 6/2013 |
| KR | 2019970038847 U | 7/1997 |

OTHER PUBLICATIONS

May 12, 2017 Extended Search Report issued in European Patent Application No. 14856546.8.

Jan. 27, 2015 International Search Report issued in International Patent Application No. PCT/JP2014/078213.

* cited by examiner

FIG. 1

DOWNSTREAM SIDE ← UPSTREAM SIDE

CLEAN WORK DEVICE

TECHNICAL FIELD

The present invention relates to a clean work device.

BACKGROUND ART

Regenerative medicine that cultures the cells of a patient and implants the cells in, for example, a portion missing from the body of the patient has come to attention. In general, the work to cultivate the cells is performed in a clean environment using a clean work device that can maintain the clean environment, such as a safety cabinet, a clean bench, or an isolator. In addition, various studies have been made for equipment that provides a clean environment, such as a clean work device (refer to PTLs 1 and 2). PTL 1 describes a local air cleaning device having a pair of push hoods disposed therein so that the airflow opening surfaces of the push hoods face each other and two airflows hit each other. PTL 1 claims that such a mechanism can provide a clean air space having a high cleanliness without having an enclosure. In addition, PTL 2 describes a device that defines a space above placement unit, such as an autopsy table, as a zone representing a clean area and diagonally blows air to the zone from the upper right and left side of the immediately above area of the zone. The blown air is sucked through a suction port. PTL 2 claims that such a device can increase the cleanliness in the zone. In addition, aerosol generated by a specimen can be prevented from entering the zone and, thus, a surgeon can be protected from being infected by aerosol.

CITATION LIST

Patent Literature

PTL 1: JP 2008-275266 A
PTL 2: JP 2005-201488 A

SUMMARY OF INVENTION

Technical Problem

When cells to be used for regenerative medicine are cultivated and if the cells of different persons are simultaneously handled in the same work area, there is a risk of cross-contamination that contaminates one ceil due to, for example, a bacteria attached to the other cell. To prevent such cross-contamination, the cells of different persons have not been handled in the same work area, or the work area has been cleaned by, for example, decontamination, disinfection, and sterilization. In addition, to reduce the risk of cross-contamination more when cells to be handled are switched to other cells, it is desirable that the surrounding area of the work area through which the cells are carried in the work area pass be also cleaned.

However, according to PTL 1, two airflows hit each other and flow to the outside of a clean air apace (a work area). Accordingly, if the technique is used for cell culture, aerosol and airborne droplets. For example, generated inside the work area are expelled to the surrounding area and, thus, the surrounding area is likely to be contaminated, depending on the type of the cell to be handled. Consequently, each time a cell to be handled is switched to another cell, the surrounding area needs to be cleaned in addition to the work area. In contrast, according to PTL 2, aerosol and airborne droplets are less likely to be expelled to the surrounding area and, thus, the surrounding area need not be cleaned. However, each time a cell to be handled is switched to another cell, the work area needs to be cleaned. Accordingly, removal of such a troublesome operation has been desired.

Accordingly, it is a main object of the present invention to provide a clean work device capable of reducing a troublesome operations, such as decontamination, disinfection, and sterilization, when an object, such as a cell, is switched to another object.

Solution to Problem

To achieve the above-described main object of the invention, a clean work device of the present invention is constructed as follows.

The present invention provides a clean work device for use in a predetermined work sequentially performed on different objects, comprising: a work area disposed in a conveyance path of the object, the work area having an inlet and an outlet in the conveyance path, a downflow air curtain being provided at least at the inlet and the outlet, the downflow air curtain blowing out of an air outlet port and being sucked by an air suction port that faces the air outlet port; a moving unit for repeatedly performing an operation that moves a placement surface oil which the object is placed from the inlet side of the work area into the work area and, thereafter, moves the placement surface from an outlet side of the work area to the outside of the work area and, subsequently, moves back the placement surface to the inlet side again; and a cleaning unit for cleaning the placement surface during a period of time from when the moving unit moves the placement surface to the outside of the work area until the moving unit moves back the placement surface to the inlet side of the work area.

In the clean work device, after the predetermined work is completed, the placement surface is cleaned by the cleaning unit during a period of time from when the placement surface moves from the outlet side of the work area to the outside of the work area until the placement surface moves back to the inlet side of the work area. Thereafter, the placement surface is used as a clean placement surface. Since the placement surface is automatically cleaned in this manner, the need for individually cleaning the placement surface each time an object is switched can be eliminated. In addition, since the predetermined work, such as the culture medium replacement, is performed in the work area that is partitioned by the downflow air curtain, aerosol and airborne droplets, for example, generated during the predetermined work are less likely to leak out into the conveyance path outside the work area. Accordingly, a troublesome operation related to cleaning can be reduced in total. Note that as used herein, the term "cleaning" refers to decontamination, disinfection, and sterilization, that is, clearing the toxicity by killing or eliminating, for example, microbes so that the microbes do not harm other living organisms or become non-infectious. The level of cleanliness can be set to a desired level.

In the clean work device of the present invention, the work area may have the inlet on the upstream side of the conveyance path and the outlet on the downstream side of the conveyance path. In the clean work device of the invention, the work area may have the inlet that is the same as the outlet.

The clean work device of the present invention may further include a clean area that includes the work area. In this manner, it is possible that predetermined work that may generate, for example, aerosol and the airborne droplet is performed in the work area, while work, which requires a clean environment, other than the predetermined work and an equipment storing operation are performed in the clean area outside the predetermined area. At that time, since aerosol and airborne droplets generated during determined work are less likely to leak out into the clean area outside the work area, the clean area can be easily maintained to be clean.

In the clean work device of the present invention, the entire periphery of the work area may be surrounded by the air curtain. In this manner, the work area air curtain functions as a wall. Since the work area does have a wall, the wall surface need not be cleaned. Consequently, the need for an additional troublesome cleaning operatic can be eliminated.

In the clean work device of the present invention, the moving unit may repeatedly perform an operation that moves the placement surface along an upper horizontal lane including the work area in a predetermined direction, turns over and leads the placement surface to a lower horizontal lane that faces the upper horizontal lane, moves the placement surface along the lower horizontal lane in a direction opposite to the predetermined direction, and turns over and leads the placement surface to the upper horizontal lane. In this manner, a space required in the horizontal direction can relatively reduced. In the clean work device, an upstream-side moving unit may be disposed on the upstream side of the moving unit to be adjacent to the moving unit with the air curtain provided for the inlet of the work area therebetween. In this manner, the belt of the upstream-side moving unit does not pass through the work area. Thus, aerosol and airborne droplets, for example, generated during the predetermined work are prevented from leaking out into the conveyance path outside the work area more certainly. In addition, in the clean work device, a downstream-side moving unit may be disposed on the downstream side of the moving unit so as to be adjacent to the moving unit with the air curtain provided for the outlet of the work area therebetween. In this manner, the belt of the downstream-side moving unit does not pass through the work area. Thus, aerosol and airborne droplets, for example, generated during the predetermined work are prevented from leaking out into the conveyance path outside the work area more certainly.

In the clean work device of the present invention, the moving unit may repeatedly perform an operation that moves the placement surface along a first horizontal lane including the work area in a predetermined direction, turns the placement surface around toward a second horizontal lane that is in the same plane as the first horizontal lane, moves the placement surface along the second horizontal lane in a direction opposite to the predetermined direction, and turns the placement surface around toward the first horizontal lane. In this manner, a space required in the height direction can be relatively reduced.

In the clean work device of the present invention, the moving unit may be a conveyor using a belt, and the belt may have an air passage in a portion thereof that is located between the air outlet port and the air suction port that face each other when the belt is positioned at a predetermined work position. In this manner, when the belt, is positioned at a predetermined work position, that is, when the predetermined work is performed, a downflow air curtain is formed via the air passage without being blocked by the placement surface disposed between the air outlet port and the air suction port that face each other.

In the clean work device of the present invention, downflow air that is weaker than the air curtain may flow in the work area. In this manner, aerosol and airborne droplets generated during the predetermined work can be prevented more certainly.

DESCRIPTION OF EMBODIMENTS

Figure 1:
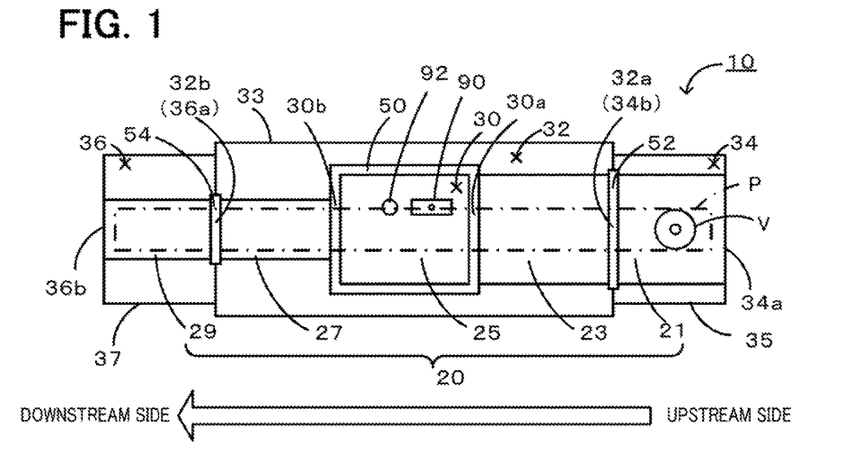
FIG. 1 is a plan view schematically illustrating the structure of a clean work device 10.
Figure 2:
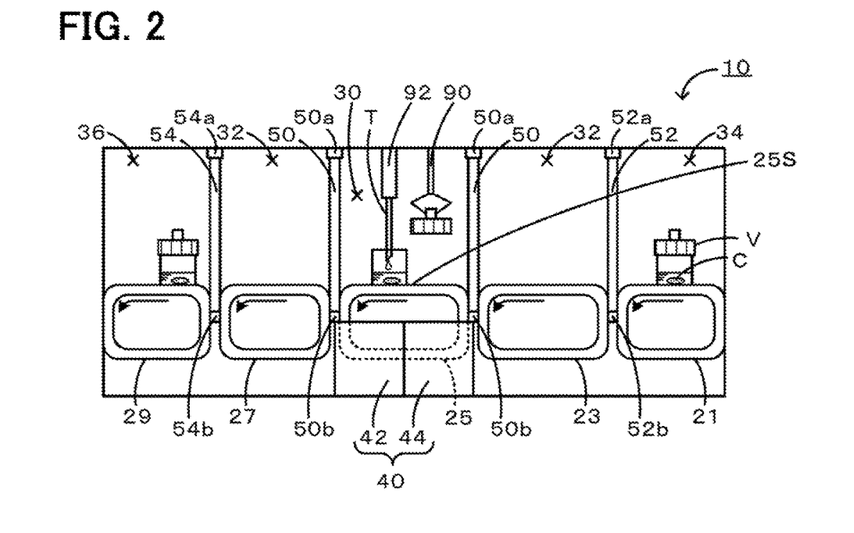
FIG. 2 is a front view schematic illustrating the structure of the clean work device 10.
Figure 3:
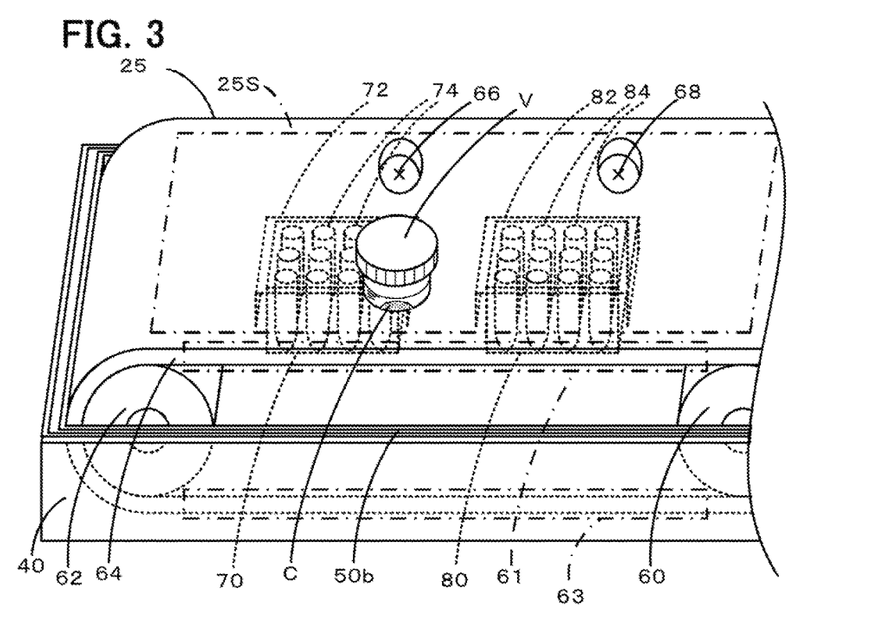
FIG. 3 is a perspective view schematically illustrating the structure of a work area 30 and its vicinity.
Figure 4:
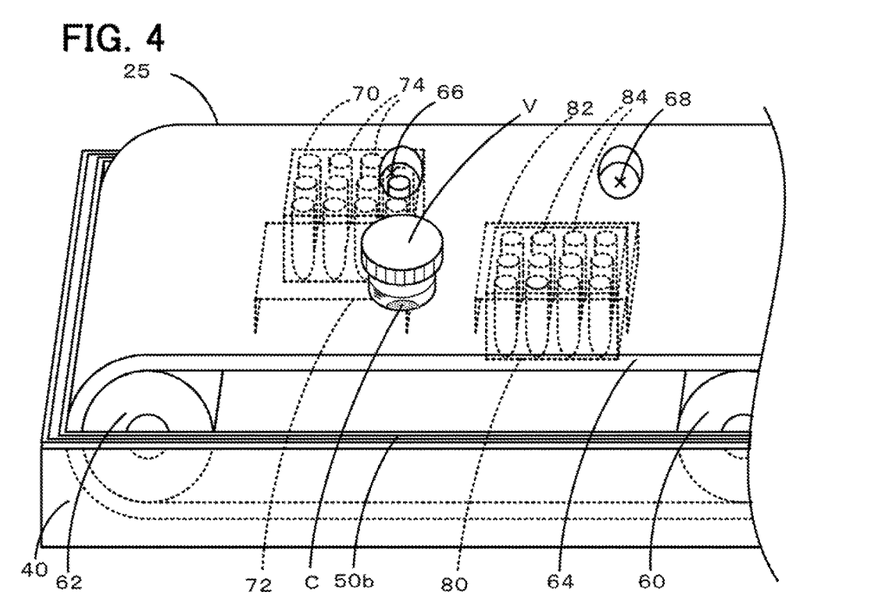
FIG. 4 is a perspective view schematically illustrating the structure of the work area 30 and its vicinity.

An exemplary embodiment of the present invention is described below with reference to the accompanying drawings. FIG. 1 is a plan view schematically illustrating the structure of a clean work device 10. FIG. 2 is a front view schematically illustrating the structure of the clean work device 10. In addition, FIGS. 3 and 4 are perspective views schematically illustrating the structure of the vicinity of a work area 30 and its vicinity.

The clean work device 10 serves as a culturing facility used to sequentially conduct culture work (corresponding to predetermined work of the present invention) on different cells C (corresponding to an object of the present invention). The clean work device 10 includes the work area 30 provided in the middle of a conveyance path P for the cells C, a conveyor group 20 that constitutes the conveyance path P, and a cleaning device 40 disposed under the work area 30. The cells C are stored in a culture vessel V, and the cells C are transferred together with the culture vessel V.

The work area 30 is provided in the conveyance path P for the cells C. The work area 30 has an inlet 30a on the upstream side of the conveyance path P and an cutlet 30b on the downstream side of the conveyance path P. The work area has a work area air curtain 50 throughout the periphery thereof including the inlet 30a and the outlet 30b. The work area air curtain 50 is a push-pull air curtain formed by downflow air that blows out of an air outlet port 50a disposed above the work area 30 and is sucked by en air suction port 50b that faces the air outlet port 50a. Clean air that has passed through, for example, a HEPA filter or a ULPA filter blows out of the air outlet port 50a. In addition, the work area 30 is an area where a culture work, such as culture medium replacement for the culture vessel V, is performed and an area that requires, for example, cleanliness class 100. The entire ceiling of the work area 30 has an air outlet port disposed therein (not illustrated). The air outlet port blows out clean air that has passed through, for example, a HEPA filter or a ULPA filter. Thus, downflow air that is weaker than the work area air curtain 50 flows out of the air outlet port of the ceiling of the work area 30. In addition, the ceiling of the work area 30 has, for example, a robot arm 90 that opens or closes a cover of the culture vessel V and a liquid supply and discharge device 92 disposed thereon. The liquid supply and discharge device 92 supplies or discharges liquid serving as a culture medium. The top end of the liquid supply and discharge device 92 has a structure that allows a tip T (with a single hole in this example) used to perform pipetting to be mounted and removed. At least each time the cells C are replaced with a new one, the tip T is also replaced and used. The work area 30 is included in a clean area 32.

The clean area 32 is an area for which for example, the cleanliness that is substantially the same as that of the work area 30 is required. The clean area 32 is surrounded by a wall 33. The wall 33 has an inlet. 32a on the upstream side and an outlet 32b on the downstream side. The inlet 32a and the outlet 32b are provided with clean area air curtains 52 and 54, respectively. Like the above-described work area air curtain 50, the clean area air curtains 52 and 54 are formed by downflow air that blows out of the air outlet ports 52a and 54a and is sucked by the air suction ports 52b and 54b that face the air outlet ports 52a and 54a, respectively. In addition, clean air that has passed through, for example, a HEPA filter or a ULPA filter blows out from the air outlet ports 52a and 54a. Like the work area 30, the entire ceiling of the clean area 32 has an air outlet port (not illustrated) disposed therein. The blows out that has passed through, for example, a HEPA filter or a ULPA filter. Downflow air that is weaker than the work area air curtain 50 flows out of the air outlet port of the ceiling of the clean area 32. Buffering areas 34 and 36 are provided on the upstream and downstream sides of the clean area 32, respectively.

The buffering areas 34 and 36 provide an environment in which the cleanliness is lower than in the work area 30 and the clean area 32 and is higher than in the outside. For example, the cleanliness class 10000 is required for the buffering areas 34 and 36. The periphery of the buffering area 34 is surrounded by a wall 35. The wall 35 has an inlet 34a with a door (not illustrated) on the upstream side. In addition, the well 35 has an outlet 34b that also serves as the inlet 32a of the clean area 32 on the downstream side. Furthermore, the periphery of the buffering area 35 is surrounded by a wall 37. The wall 37 has an inlet 36a on the upstream side and an outlet 36b with a door (not illustrated) on the downstream side. The inlet 36a also serves as the outlet 32b of the clean area 32.

The conveyor group 20 includes conveyers arranged in series. The conveyors include a conveyor 25 (corresponding to a moving unit of the present invention) disposed in the work area and other conveyors disposed on the upstream and downstream sides of the conveyor 25. More specifically, an upstream conveyor 23 is disposed on the upstream side of the conveyor 25 in the work area so as to be adjacent to the conveyor 25 via the work area air curtain 50. A carry-in conveyor 21 is disposed on the upstream side of the upstream conveyor 23 so as to be adjacent to the upstream conveyor 23 via the air curtain 52. In addition, a downstream conveyor 27 is disposed on the downstream side of the conveyor 25 in the work area so as to be adjacent to the conveyor 25 via the work area air curtain 50. A carry-out conveyor 29 is disposed on the downstream side of the downstream conveyor 27 so as to adjacent to the downstream conveyor 27 via the clean area air curtain 54. Note that the air suction port 50b of the work area air curtain 50 is disposed between the upstream conveyor 23 and the conveyor 25 in the work area and between the conveyor 25 in the work area and the downstream conveyor 27 at a height level that is lower than a placement surface 25S. Similarly, the air suction ports 52h of the air curtain 52 is disposed between the carry-in conveyor 21 and the upstream conveyor 23, and the air suction port 54b of the clean area air curtain 54 is disposed between the downstream conveyor 27 and the carry-out conveyor 29 at a height level that is lower than the placement surface 25S.

The conveyor 25 in the work area moves the placement surface 25S having the cells C (contained in the culture vessel V in this example) mounted thereon from the inlet 30a side of the work area 30 into the work area stops the movement. Thereafter, the conveyor 25 moves the placement surface 25S from the outlet 30b side of the work area 30 to the outside of the work area 30. Subsequently, the conveyor 25 moves the placement surface 25S toward the inlet 30a side again and, thereafter, such operations are repeated. As illustrated in FIGS. 3 and 4, the conveyor 25 in the work area is formed by stretching a continuous belt 54 between a horizontal roller 60 the upstream side and a horizontal roller 52 on the downstream side. In the conveyor 25, the belt is moved by rotating the rollers 60 and 62 using a motor illustrated). More specifically the conveyor 25 in the work area moves the belt 64, along an upper horizontal lane 61 in a predetermined direction and turns over the belt 64 and leads the belt 64 toward a lower horizontal lane 63. Thereafter, the conveyor moves the belt 64 along the lower horizontal lane 63 in a direction opposite to the predetermined direction and turns over the belt 64 and leads the belt 64 toward the upper horizontal lane 61. The conveyor 25 repeats such operations. Note that a conveyor control unit no illustrated) is connected to the motor to control the moving direction, the moving speed and the start position and the stop position of the placement surface 25S. In the conveyor 25 in the work area, the placement surface 25S provided as part of the belt 64 and series as a workbench that allows the culture vessel V be mounted thereon and allows the culture work to be performed thereon. The placement surface 25S has a pick-up hole 66 and a waste hole 68 formed therein. The pick-up hole 66 is a hole used to pick up a tip from a tip case 70 (described below) disposed beneath the placement surface 25S. In addition, the waste hole 68 is a hole used to throw a used tip into a waste, case 80 (described below) disposed beneath the placement surface 25S.

Like the conveyor 25 in the work area, each of the carry-in conveyor 21, the upstream conveyor 23, the downstream conveyor 27, and the carry-out conveyor 29 has a continuous belt stretched between an upstream horizontal roller and a downstream horizontal roller and moves the belt by rotating the rollers using a motor.

The tip case 70 has a plurality of set holes 74 formed therein, and a plurality of tips are set in the set holes 74. In addition, the tip case 70 includes a moving unit (not illustrated) for moving the tip case 70. A control unit (not illustrated) is connected to the moving unit. The control unit is connected to the above-described conveyor control unit. The control unit controls the moving unit so as to move the tip case 70 in accordance with, for example, the position information regarding the placement surface 25S acquired from the conveyor control unit. In the present embodiment, the control unit controls the moving unit so that the tip case 70 is stored beneath a cover 72 (FIG. 3) until a predetermined pick-up timing is reached at which the placement surface 25S is positioned at a culture work position. In contrast, if the pick-up timing is reached, the control unit controls the moving unit so that a tip that is set in a desired set hole 74 is disposed beneath the pick-up hole 66 of the placement surface 25S (FIG. 4). If a predetermined pick-up end timing is reached, the tip case 70 is stored beneath the cover 72 again.

A waste case 80 has a plurality of waste holes 84 formed therein. In addition, the waste case 80 includes a moving unit (not illustrated) for moving the waste case 80. A control unit (not illustrated) is connected to the moving unit. The control unit is connected to the above-described conveyor control unit. The control unit controls the moving unit so as to move the waste case 80 in accordance with, for example, the position information regarding the placement surface 25S acquired from the conveyor control unit. In the present embodiment, the control unit controls the moving unit so that the placement surface 25S is positioned at a predetermined culture work position and, in addition, the waste case 80 is stored beneath a cover 82 until a predetermined waste timing is reached after the above-described pick-up end timing. In addition, if the waste timing is reached, the control unit controls the moving unit so that a desired waste hole 84 is located beneath the waste hole 68 of the placement surface 25S. If a predetermined waste end timing is reached, the waste case 80 is stored beneath the cover 82 again.

The cleaning device 40 (corresponding to a cleaning unit of the present invention) cleans the placement surface during a period of time from when the conveyor 25 in the work area moves the placement surface 25S to the outside of the work area 30 until the conveyor 25 in the work area moves back the placement surface 25S in the work area to the inlet 30a side of the work area 30. In the present embodiment, the cleaning device 40 is disposed so as to be adjacent to the lower horizontal lane 63 of the conveyor 25 in the work area. The cleaning device 40 includes a cleaning liquid processing chamber 42 and an ultraviolet processing chamber 44. The cleaning liquid processing chamber 42 contains, for example 36% hydrogen peroxide solution or a 6% peracetic acid solution poured thereinto. By moving the placement surface 25S through the cleaning liquid, the placement surface 25S after being used for the culture work in the work area 30 can be cleaned. The ultraviolet processing chamber 44 includes a dryer unit (not illustrated) that blows clean dry air and an ultraviolet emitting unit (not illustrated) that emits ultra violet light. By blowing dry air to the placement surface 25S and emitting ultraviolet light to the placement surface 25S, the placement surface 25S can be dried and cleaned. Note that the cleaning liquid attached in the cleaning liquid processing chamber 42 is decomposed through, for example, drying in the ultraviolet processing chamber 44.

An example of the case in which the cells C are cultured using the clean work device 10 is described below. An operator powers on the clean work device 10 and sets up the operating conditions in the control units, such as the conveyor control unit, the tip case control unit, and the waste case control unit, first. In this manner, downflow air that forms air curtains 50, 52, and 54 flows in the clean work device 10 and, thus, the clean work device 10 enters an operating mode. Subsequently, the operator prepares a plurality of sealed culture vessels V each containing the cells C, which is an objects and the culture medium. Thereafter, the operator sequentially places the culture vessels V on the carry-in conveyor 21 in the buffering area 34 through the inlet 34a at appropriate timings. Note that when the culture vessel V is placed on the carry in conveyor 21, it is desirable that the surface of each of the culture vessels V be cleaned in advance. The culture vessel V placed on the carry-in conveyor 21 advances to the downstream side of the conveyance path P and moves onto the upstream conveyor 23. Furthermore, the culture vessel V advances to the downstream side of the conveyance path P and moves onto the placement surface 25S of the conveyor 25 in the work area. At that time the culture vessel V is located on the placement surface 25S at a position adjacent to the pick-up hole 66. Thereafter, when the entire placement surface 25S is located inside the work area 30 by the movement of the belt 64 of the conveyor 25 in the work area, the movement, of the belt 64 is stopped (refer to FIG. 3, the culture work position). Subsequently, the liquid supply and discharge device 92 picks up an unused tip T from the tip case 70 and attaches the tip T to the top end during a period of time from the pick-up timing until the pick-up end timing. When the pick up end timing has been reached, the robot arm 90 opens the cover of the culture vessel V and the liquid supply and discharge device 92 replaces the culture medium in the culture vessel V with a new one. After the replacement of the culture medium is completed, the robot arm 90 closes the cover of the culture vessel V and seals the culture vessel V. Thereafter, when a predetermined waste timing is reached, the liquid supply and discharge device 92 throws the used tip into the waste case 80 before the time the waste-end timing is reached. Thus, the culture work that may generate aerosol and airborne droplets is completed.

After the culture work is completed, the conveyor 25 in the work area resumes moving the belt 64. As the belt 64 moves, the culture vessel V moves from the placement surface 25S of the conveyor 25 in the work area onto the downstream conveyor 27 and advances to the downstream side of the conveyance path P. Thereafter, the culture vessel V moves onto the carry-out conveyor 29, and advances to the downstream side of the conveyance path P. If the culture vessel V reaches the outlet 36b of the buffering area 36, the culture vessel V is picked up by the operator. In the meanwhile, after the culture work is completed, the placement surface 25S moves from the outlet 30b side of the work area 30 to the outside of the work area 30 and passes through the cleaning device 40. Thus, the placement surface 25S is cleaned. Thereafter, the placement surface 25S moves back to the inlet 30a side of the work area 30 again. Subsequently, the placement surface 25S is used again as the cleaned placement surface 25S. During a period of time during which the placement surface 25S is being cleaned in this manner, the next culture vessel V is moved by the conveyors 21 and 23 and reaches the inlet 30a of the work area 30. Thereafter, the culture vessel V moves onto the cleaned placement surface 25S and is located within the work area 30. Subsequently, in the same manner as described above, culture work and additional works are performed. By repeating such operations, the culture work for different objects can be sequentially performed in the clean work device 10.

According to the clean work device 10 of the above-described embodiment, after the culture work is completed, the placement surface 25S is cleaned y the cleaning device 40 during a period of time from when the placement surface 25S is moved to the outside of the work area 30 until the placement surface 25S is moved back to the inlet 30a side of the work area 30. Thereafter, the placement surface 25S is used as the cleaned placement surface 25S again. Since the placement surface 25S is automatically cleaned in this manner, the need for individually cleaning the placement surface 25S each time an object is switched can be eliminated and, thus, a risk of the cross-contamination is low. In addition, since the culture work, such as the culture medium replacement, is performed in the work area that is partitioned by the downflow work area air curtain 50, aerosol and airborne droplets generated during the couture work are less likely leak out into the conveyance path P outside the work area. Accordingly, a risk of biohazard that spreads contamination is low.

Since the clean area 32 that includes the work area 30 is provided, it is possible that the culture work that may generate, for example, aerosol and the airborne droplet is performed in the work area 30, while work other than the culture work, which requires a clean environment, and an equipment storage are performed in the clean area 32 outside the work area 30. At that time, since aerosol and airborne droplets generated during the culture, work are less likely to leak out into the clean area outside the work area, the clean area can be easily maintained to be clean. In addition, since the clean area 32 is located between the work area 30 and the external environment, a contaminating material in the external environment is less likely to enter the work area 30 and, thus, the work area 30 can be maintained to be clean more certainly. Furthermore, since the buffering areas 34 and 36 are provided or the upstream side and the downstream side of the clean area 32, respectively, the clean area 32 is not directly exposed to the outside and, thus, the work area 30 and the clean area 32 can be easily maintained to be clean.

In addition, the entire periphery of the work area 30 is surrounded by the work area air curtain 50. Accordingly, the work area air curtain 50 fractions as a wall. Since the work area 30 does not have a wall, the wall surface need not be cleaned. Consequently, the need for an additional troublesome cleaning operation can be eliminated.

In addition, the conveyor 25 in the work area repeats the following operation. That is, the conveyor 25 moves the placement surface 25S along the upper horizontal lane 61 including the work area 30 in a predetermined direction. Thereafter, the conveyor 25 turns over the placement surface 25S to the lower horizontal lane 63 that faces the upper horizontal lane 61. Subsequently, the conveyor 25 in the work area moves the placement surface 25S along the lower horizontal lane 63 in a direction opposite to the predetermined direction and turns over the placement surface 25S to the upper horizontal lane 6*l*. Accordingly, a space required in the horizontal direction can be relatively reduced.

In addition, the upstream conveyor 23 is provided on the upstream side of the conveyor 25 in the work area so as to be adjacent to the conveyor 25 in the work area with the work area air curtain 50 therebetween. Furthermore, the downstream conveyor 27 is provided on the downstream side of the conveyor 25 in the work area so as to be adjacent to the conveyor 25 in the work area with the work area air curtain 50 therebetween. Accordingly, the belt surfaces of the upstream conveyor 23 and the downstream conveyor 27 do not pass through the work area 30. Thus, aerosol and airborne droplets, for example, generated during the culture work are prevented from leaking out into the conveyance path P outside the work area 30 more certainly.

In addition, the air suction port 50*b* is disposed beneath the outer peripheral of the placement surface 25S, and the air outlet port 50*a* is disposed on the ceiling that faces the air suction port 50*b*. Accordingly, the belt 64 is not located between the air outlet port 50*a* and the air suction port 50*b* that face each other and, thus, the need for providing, for example, an air passage in the belt 64 can be eliminated. Furthermore, the air suction port 52*b* is provided between the carry-in conveyor 21 and the upstream conveyor 23, and the air outlet port 52*a* is provided in the ceiling that faces the air suction port 52*b*. Accordingly, no belt is disposed between the air outlet port 52*a* and the air suction port 52*b* that face each other and, thus, the need for providing, for example, an air passage in the belts of the conveyor 21 and the upstream conveyor 23 can be eliminated. In addition, the air suction port 54*b* is provided between the downstream conveyor 27 and the carry-out conveyor 29, and the air outlet port 54*a* is provided in the ceiling that faces the air suction port 54*b*. Accordingly, no belt is disposed between the air outlet port 54*a* and the air suction port 54*b* that face each other and, thus, the need for providing, for example, an air passage in the belts of the downstream conveyor 27 and the carry-out conveyor 29 can be eliminated.

In addition, downflow air that is weaker than the work area air curtain 50 flows in the work area 30. Accordingly, aerosol and airborne droplets, for example, generated during the culture work can be reduced more. Furthermore, downflow air that is weaker than the work area air curtain 50 flows in the clean area 32. Accordingly, any substance in the air can be reduced in the clean area 32 and, thus, the clean area 32 can be maintained to be clean more certainly.

In addition, the robot arm 90 that performs the work, such as opening and closing of the cover of the culture vessel V, and the liquid supply and discharge device 92 that supplies and discharges liquid, such as a culture medium, are hung from the ceiling of the work area 30. The placement surface 25S has the pick-up hole 66 and the waste hole 68 formed therein and is configured to allow a tip to be taken out through the pick-up hole 66 and to be thrown into the waste hole 68. Accordingly, the work performed by the liquid supply and discharge device 92, such as tip replacement and culture medium replacement, can be completed within the work area 30 and, thus, the aerosol and airborne droplets, for example, generated during the culture work are less likely to leak out into the conveyance path P outside the work area 30.

It should be noted that the present invention is not limited to the above-described embodiment in any way, and a variety of alternative embodiments are possible without departing from the spirit and scope of the invention.

Figure 5:
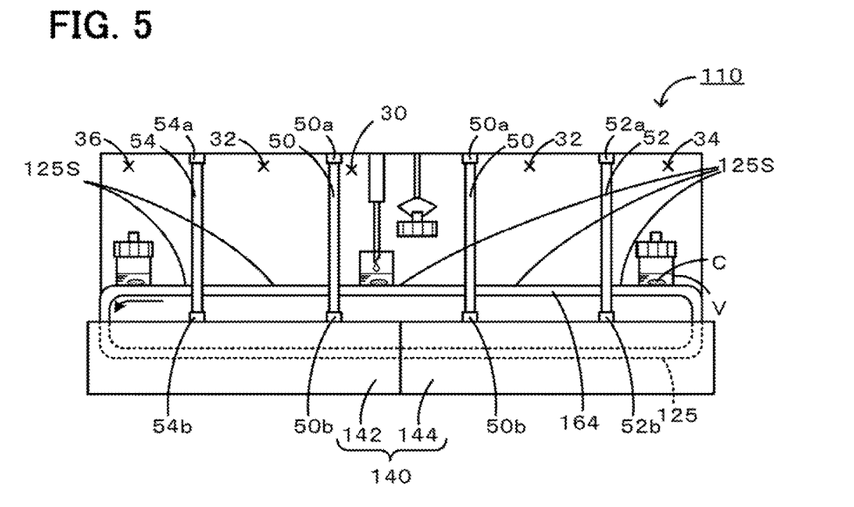
FIG. 5 is front view schematically illustrating the structure of a clean work device 110.

For example, while the above embodiment has been described with reference to the conveyor 25 in the work area, the upstream conveyor 23 and the carry-in conveyor 21 on the upstream side of the conveyor 25, and the downstream conveyor 27 and the carry-out conveyor 29 on the downstream side of the conveyor 25, the structure of the conveyors is not limited thereto. For example, some of the conveyors may be replaced with a continuous conveyor. Alternatively, all the conveyors may be replaced with a continuous conveyor. A clean work device 110 according to such a modification is illustrated in FIG. 5. Note that the same constituent elements of the clean work device 110 as those of the clean work device 10 are designated by the same reference numerals, and descriptions of the constituent elements are not repeated. The clean work device 110 includes a single continuous conveyor 125 (corresponding to a moving unit of the present invention) instead of the conveyor group 20. Like the conveyor 25 in the work area, the conveyor 125 has a belt 164 stretched between an upstream horizontal roller and a downstream horizontal roller in continuous manner, and the belt 164 is moved by rotating the rollers using a motor. In addition, the clean work device 110 has a cleaning device 140 disposed beneath the work area 30 the clean area, and the buffering areas 34 and 36. The cleaning device includes cleaning liquid processing chamber 142 and an ultraviolet processing chamber 144. Note that the cleaning device 140, the cleaning liquid processing chamber 142, and the ultraviolet processing chamber 144 have structures that are the same as those of the cleaning device 40, the cleaning liquid processing chamber 42, and the ultraviolet processing chamber 44 of the clean work device 10, respectively, except that they extend to the positions below the clean area 32 and the buffering areas 34 and 36. Accordingly, detailed description is not given herein. The clean work device 110 having such a structure has the belt 164 between the air outlet port 50a and the air suction port 50b that faces the air outlet port 50a. Accordingly, if the belt 164 disposed between the air outlet port 50a and the air suction port 50b that face each other does not have air permeability, the downflow of the air curtain is blocked by the belt 164 and, thus, may flow toward the inside and the outside of the work area 30. Consequently, the belt 164 has an air passage in a portion located between the air outlet port 50a and the air suction port 50b that face each other when the belt 164 is placed at a predetermined position. Since the clean work device 110 has such an air passage, a downflow air curtain is formed, passing through the air passage without being interfered by the placement surface 125S located between the air outlet port 50a and the air suction port 50b that face each other when the placement surface 125S is placed at a predetermined culture work position, that is, during a culture work. Examples of the belt 164 having the air passage therein include a mesh shaped belt and a belt having a through hole, such as a slit, therein. Note that if the clean work device 110 includes the belt 164 having a though-hole, such as a slit, therein, the conveyor control unit controls the motor so that the placement surface 125S is maintained to be stationary at the predetermined culture work position during a culture work.

Figure 6:
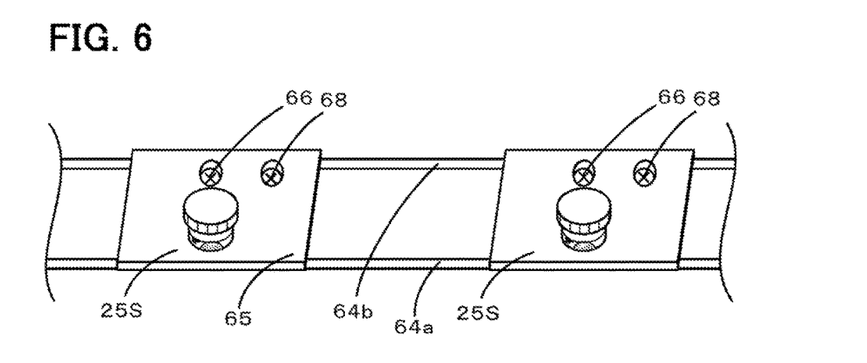
FIG. 6 is a perspective view of an example of a conveyor 125 in the work area.

While the above embodiment has been described with reference to the conveyor 25 in the work area having the placement surface 25 provided in the belt 64 with large width (FIGS. 3 and 4), the conveyor 25 is not limited to such a structure. For example, as illustrated in FIG. 6, two belts, that is, belts 64a and 64b each having a small width may be disposed so as to be separated from each other instead of the belt 64. A palette 65 that fixedly bridges between the belts 64a and 64b may be used as the placement surface 25S. Note that in such a case, the distance between the neighboring palettes 65 can function as the above-described air passage. In addition, while the above embodiment has been described with reference to the conveyor 25 in the work area formed as a belt conveyor, the conveyor 25 in the work area is not limited to a belt conveyor.

While the above embodiment has been described with reference to the placement surface 25S having the pick-up hole 56 and the waste hole 68 therein, the placement surface 25S need not have the holes. Alternatively, the placement surface 25S may have a pick-up and waste hole that serves as both the pick-up hole 66 and the waste hole 68. In addition, the placement surface 25S may include, for example, a mount concave portion or a mount convex portion used to mount the culture vessel V. At that time, the mount concave portion or the mount convex portion may include a fixing mechanism for preventing the culture vessel V from moving and rotating during the culture work. The fixing mechanism may be processed so as to be non-skid. Alternatively, the fixing mechanism may have a concave or a convex that mates with the convex or the concave provided on the culture vessel V.

Figure 7:
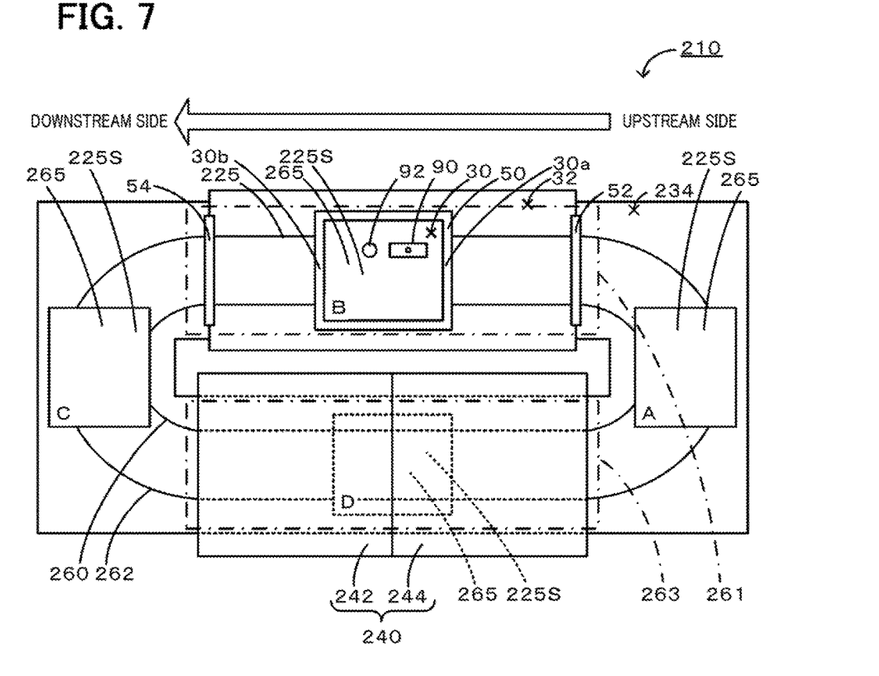
FIG. 7 is a plan view schematically illustrating the structure of a clean work device 210.

In addition, instead of the conveyor 25 in the work area, a conveyor 225 (corresponding to a moving unit of the present invention) illustrated in FIG. 7 may be employed. FIG. 7 is a plan view schematically illustrating the structure of a clean work device 210 according to the modification. Note that the same constituent elements of the clean work device 210 as those of the clean work device 10 are designated by the same reference numerals, and descriptions of the constituent elements are not repeated. The clean work device 210 includes a conveyor 225. As illustrated in FIG. 7, the conveyor 225 includes an inner peripheral rail 260 and an outer peripheral rail 262. A palette 265 serving as a placement surface 225S is mounted on drive wheels not illustrated) provided on the inner peripheral rail 260 and the outer peripheral rail 262. By rotating the drive wheels using a motor not illustrated), the conveyor moves the palette 265. More specifically, the conveyor 225 moves the palette 265 along a first horizontal lane 261 in a predetermined direction. Thereafter, the conveyor 225 turns the palette 265 around toward a second horizontal lane 263 that is in the same plane as the first horizontal lane 261. Subsequently, the conveyor 225 moves the palette 265 along the second horizontal lane 263 in a direction opposite to the predetermined direction. Thereafter, the conveyor 225 turns the palette 265 around toward the first horizontal lane 261. Such operations are repeated. The clean work device 210 includes a continuous buffer area 234 that connects the downstream side to the upstream side of the clean area 32. In addition, the clean work device 210 includes a cleaning device 240 having a cleaning liquid processing chamber 242 and an ultraviolet processing chamber 244 in the middle of the buffer area 234. In the clean work device 210, the culture vessel V mounted on the palette 265 at a predetermined mount position in the buffer area 234 (e.g., a position A in FIG. 7) is moved to the work area 30 through the clean area 32 by the operation of the conveyor 225. When the palette 265 is positioned within the work area 30 at the culture work position (e.g., a position B in FIG. 7), the conveyor 225 stops operating, and the culture work is performed. After the culture work is completed, the conveyor 225 starts operating again. The culture vessel V mounted on the palette 265 is moved from the work area 30 to the clean area 32 and then, is moved to the buffer area 234. The culture vessel V is taken out in the buffer area 234 at a predetermined take-out position (e.g., a position C in FIG. 7). Subsequently, the palette 265 having no culture vessel V mounted thereon is continuously moved to the cleaning device 240 and is cleaned at a predetermined cleaning position a position D in FIG. 7). Thereafter, the palette 265 is moved back to the mount position again. Subsequently, the palette 265 serves as a cleaned placement surface 225S again, and the next culture vessel V is mounted on the placement surface 225S. In the clean work device 210, by repeating such operations, the culture work of different objects can be sequentially performed. Note that one or more portions each having the same structure as the clean area 32, the buffering area 34, and the cleaning device 240 may be provided in the middle of the buffer area 234. Note that a conveyor having a form other than the above-described form may be employed as the conveyor 225.

Figure 8:
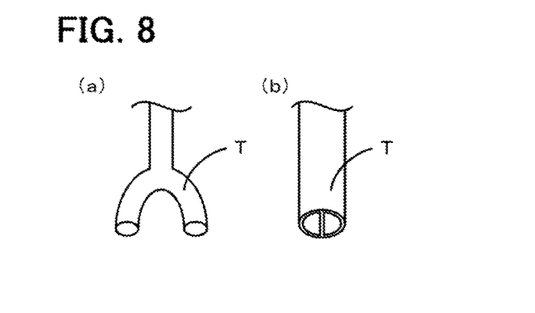
FIG. 8 is a perspective view schematically illustrating the structure of a tip T.

While the above embodiment has been described with reference to the clean work device 10 including the robot arm 90 and the liquid supply and discharge device 92, the need for the robot arm 90 and the liquid supply and discharge device 92 may be eliminated. For example, the clean work device 10 may be configured as a glove box that has the wall 33 with a hole connectable to a glove in an airtight manner and that allows an operator to work via the glove connected to the hole. While the above embodiment has been described with reference to the clean area air curtains 52 and 54, a physical shutter mechanism may be provided instead of the clean area air curtains 52 and 54. While the above embodiment has been described with reference to an operator who mounts the culture vessel V in the buffering area 34 and takes out the culture vessel V from the buffering area 36, the culture vessel V may be mounted and taken out by, for example, a robot arm instead of the operator. For example, loading and unloading of the culture vessel V between the clean work device 10 and, for example, an incubator connected to the clean work device 10 may be automatically performed. In addition, while the above embodiment has been described with reference to the robot arm 90 and the liquid supply and discharge device 92 disposed within the work area 30, the robot arm 90 and the liquid supply and discharge device 92 may be disposed in the clean area 32 outside the work area 30. Furthermore, while the above embodiment has been described with reference to the tip case 70 disposed under the placement surface 25S, the tip case 70 may be disposed in a space above the clean area 32 or in the clean area 32, for example. Note that if downflow air flows in the work area 30 and the clean area 32, the space above the work area 30 and the clean, area 32 contain few aerosol and airborne droplets and, thus, is cleaner. Accordingly, it is desirable that the robot arm 90, the liquid supply and discharge device 92, and the tip case 70 be disposed as far towards the upper side as possible. In addition, while the above embodiment has been described with reference to the tip T having a single hole, the tip T may have two holes, as illustrated in FIGS. 8(*a*) and 8(*b*), or a large number of holes. In this manner, liquid can be supplied and discharged to and from the culture vessel V by using a single tip, or a plurality of types of liquid can be supplied using a single tip. Thus, the culture work can be efficiently performed. For example, the number of tip replacements can be reduced.

While the above embodiment has been described with reference to the work area 30 having the periphery surrounded by the work area air curtain 50, the work area air curtain 50 can be provided at least at the inlet 30a and the outlet 30b. For example, the work area 30 may be partitioned by the work area air curtain 50 from the upstream side and the downstream side of the conveyance path P, and Both ends may be separated from the outside by walls. Even in such a structure, since the culture work, such as culture medium replacement, is performed in the work area 30 partitioned by the downflow work area air curtain 50, aerosol and airborne droplets, for example, generated during the culture work are less likely to leak out into the conveyance path P outside the work area. In such a case, it is desirable that the width of the work area air curtain 50 (the length in a direction perpendicular to the conveyance path P) be sufficiently large so that the aerosol and airborne droplets, for example, generated during the culture work fall short of the wall. In addition, in this case, the work area air curtain 50 may be formed by an airflow flowing in the front-rear direction (a direction that perpendicularly crosses the conveyor group 20). While the above embodiment has been described with reference to the work area 30 in which downflow air that is weaker than the work area air curtain 50 flows, the downflow air may be as strong as the work area air curtain 50, or no downflow air may flow in the work area 30.

While the above embodiment has been described with reference to the clean area 3 and the work area 30 included in the clean area 32, there is no need to provide the clean area 32. Even in such a structure, since the work area 30 is partitioned from an area outside the work area by the work area air curtain 50, the aerosol and airborne droplets, for example, generated during the culture work are less likely to leak out from the work area 30 to the outside of the work area 30. Accordingly, even if the outside of the work area 30 is not cleaned each time the object is replaced with a new one, the effect of the aerosol and airborne droplets generated during the culture work on the outside of the work area 30 negligibly remains.

While, the above embodiment has been described with reference to the air suction ports 50b, 52b, and 54b disposed at a lower height level than the placement surface 25S, the air suction ports 50b, 52b, and 54b may be disposed at the same height level as the placement surface 25S.

While the above embodiment has been described with reference to the cleaning device 40 including the cleaning liquid processing chamber 42 and the ultraviolet processing chamber 44, any other element that provides a desired cleanliness can be employed instead of such chambers. In addition, while the above embodiment has been described with reference to the cleaning device 140 disposed only under the conveyor 25 in the work area, the cleaning device 140 may be disposed under each or some or all of the conveyor 21, the upstream conveyor 23, the downstream conveyor 27, and the carry-out conveyor 29.

While the above embodiment has been described with reference to the conveyor 25 in the work area in which the placement surface 25S is moved from the upstream side to the downstream side, the placement surface 25S need not be moved from the upstream side to the downstream side at all times. The placement surface 25S may be moved from the downstream side to the upstream side as needed.

In the above-described embodiment, a plurality of the culture vessels V may be mounted on the placement surface 25S. Even in such a case, the risk of the cross-contamination can be removed if, for example, the objects are taken from the same specimen.

While the above embodiment has been described with reference to the object being a cell, the object may be a virus or a bacteria. In addition, while the above embodiment has been described with reference to the clean work device 10 being the culturing facility and the predetermined work being culture work, the predetermined work is not limited to the work related to for example, cell culture work. The predetermined work may be any work that requires maintenance of the cleanliness and prevention of expansion of contamination.

While the above embodiment has been described with reference to the work area having the inlet on the upstream side of the conveyance path and the outlet on the downstream side of the conveyance path, the work area may have an inlet and outlet that serves as both an inlet and an outlet in the middle of the conveyance path. That is for the work area, the inlet and the outlet may be the same. Note that it is desirable that the cleanliness of the inlet side of the work area be higher than that of the outlet side. In this respect, it is desirable that the inlet be provided separately from the outlet. A modification that provides an inlet and outlet that serves as both an inlet and an outlet is described below with reference to the accompanying drawings. As a modification in which an inlet and cutlet that serves as both an inlet and an outlet is provided, the clean work device 210 (refer to FIG. 7) may have the inlet 30a that is defined as a first inlet and outlet 30a and the outlet 30b that is defined as a second inlet and outlet 30b, for example. In an example described below, the culture vessel V that passes through the first inlet and outlet 30a is defined as a culture vessel V1, the culture vessel V that passes through the second inlet and outlet is defined as a culture vessel V2, and a cell is cultivated using the clean work device 210. The example is described below. In the clean work device 210, the culture vessel V1 mounted on the palette 265 at, for example, a predetermined mount position (A) passes through the clean area 32 and the first inlet and outlet 30a and reaches the work area 30 due to the movement of the conveyor 225. If the palette 265 is placed within the work area 30 at a predetermined position (B), the conveyor 225 stops operating, and the culture work is performed. After the culture work is completed, the conveyor 225 starts moving in a direction opposite to the previous direction. The culture vessel V1 mounted on the palette 265 passes through the first inlet, and outlet 30a from the work area 30 and moves from the clean area 32 to the buffer area 234. Thereafter, the culture vessel V1 is taken out at a take-out position (A) that is the same as the above-described mount position. Subsequently, the palette 265 without the culture vessel V1 placed thereon continuously moves to the cleaning device 240 and is cleaned at a predetermined cleaning position (D). After the cleaning operation is completed, the conveyor 225 starts moving in a direction opposite to the previous direction and moves back to the mount position (A) again. Subsequently, the next culture vessel V1 is mounted on the cleaned placement surface 225S. In addition, when the culture vessel V1 is taken out at the take-out position (A), a culture vessel V2 is mounted on the palette 265 at a predetermined mount position (C). The mounted culture vessel V2 passes through the clean area 32 and the second inlet and outlet 30b and reaches the work area 30 due to the movement of the conveyor 225. If the palette 265 is placed within the work area 30 at the predetermined position (B), the conveyor 225 stops operating, and the culture work is performed. After the culture work is completed, the conveyor 225 starts moving in a direction opposite to the previous direction. The culture vessel V2 mounted on the palette 265 passes through the second inlet and outlet 30b from the work area 30 and moves from the clean area 32 to the buffer area 234. Thereafter, the culture vessel V2 is taken out at a take-out position (C) that is the same as the above-described mount position. Subsequently, the palette 265 without the culture vessel V2 placed thereon continuously moves to the cleaning device 240 and is cleaned at a predetermined cleaning position (D). After the cleaning operation is completed, the conveyor 223 starts moving in a direction opposite to the previous direction and moves back to the mount position (C) again. Subsequently, the next culture vessel V2 is mounted on the cleaned placement surface 225S. At that time, the work for the culture vessel V1 and the work for the culture vessel V2 are simultaneously performed as follows:

the culture vessel V1: Mounting (A)→Culture or (B)→Taking-out (A)→Cleaning (D)→Mounting (A)→ . . . and the culture vessel V2 Taking-out (C)→Cleaning (D)→Mounting (C)→Culture work (B)→Taking-out (C)→ . . .

Note that the conveyor 225 moves the palette 265 along the first horizontal lane 261 in a predetermined direction and, subsequently, moves the palette 265 in the direction opposite to the predetermined direction. Thereafter, the conveyor 225 turns the palette 265 around toward the second horizontal lane 263 and moves the palette 265 along the second horizontal lane 263 in the predetermined direction and, subsequently, moves the palette 265 in the direction opposite to the predetermined direction. Thereafter, the conveyor 225 turns the palette 265 around toward the first horizontal lane 261. The conveyor 225 repeatedly performs the above-described operation. Also note that the clean work device 210 may use only one of the first inlet and outlet 30a and the second inlet and outlet 30b.

Figure 9:
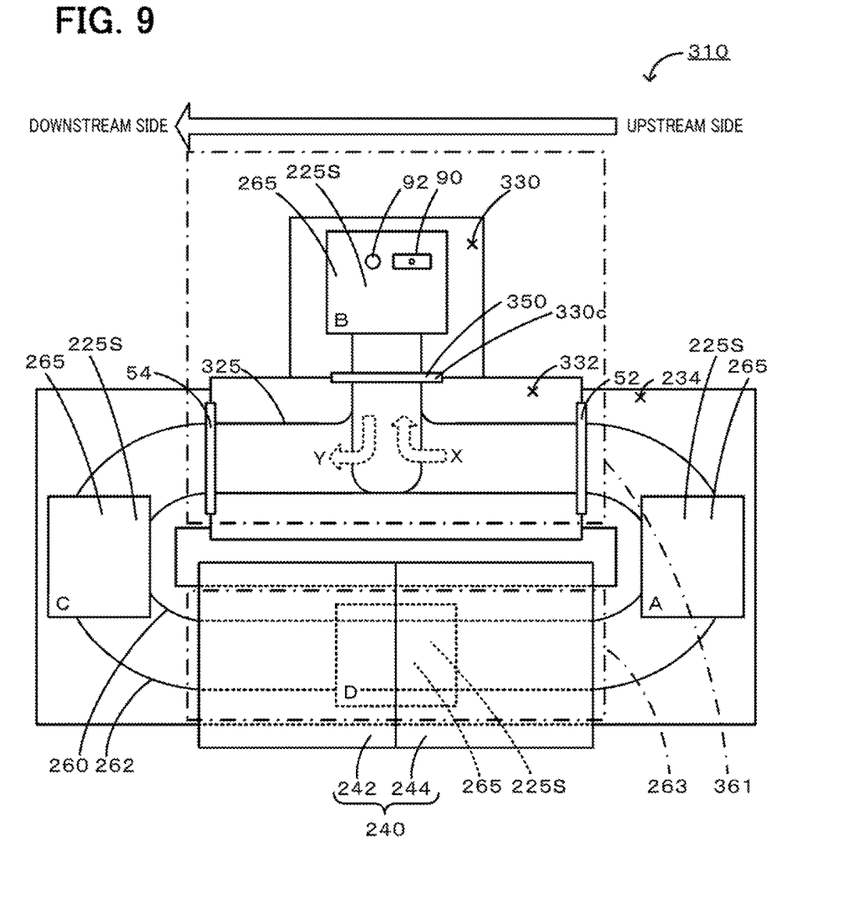
FIG. 9 is a plan view schematically illustrating the structure of a clean work device 310.

In addition, as a modification that provides an inlet and outlet that serves as both an inlet and an outlet, structure illustrated in FIG. 9 may be employed, for example. FIG. 9 is a plan view schematically illustrating the structure of a clean work device 310 according to the modification. Note that the same constituent elements of the clean work device 310 as those of the clean work device 210 are designated by the same reference numerals, and descriptions of the constituent elements are not repeated. As illustrated in FIG. 3, a work area 330 of the clean work device 310 includes an inlet and outlet 330c that serves as both an inlet and an outlet. An air curtain 350 is provided at the inlet and outlet 330c. In addition, the clean work device 310 is configured so that a conveyor 325 can move the palette 265 including the placement surface 225S between a clean area 332 and the work area 330. The conveyor 325 moves the palette 265 along a first horizontal lane 261 in a predetermined direction. Thereafter, the conveyor 325 turns the palette 265 around toward a second horizontal lane 463. Subsequently, the conveyor 325 moves the palette 265 along the second horizontal lane 263 in a direction opposite to the predetermined direction. Thereafter, the conveyor 325 turns the palette 265 around toward the first horizontal lane 261. The conveyor 325 repeats such operations. In addition, while moving the palette 265 along the first horizontal lane 261 in the predetermined direction, the conveyor 325 carries in the palette 25S from the clean area 332 into the work area 330 through the inlet and outlet 330c, as indicated by an arrow X in FIG. 9. Thereafter, the conveyor 325 carries out the palette 265 from the work area 330 into the clean area 332 through the inlet and outlet 330c, as indicated by an arrow Y. Note that the clean work device 310 may carry in and out the palette 265 so that the palette 265 moves back and forth along the arrow X or the arrow Y illustrated in FIG. 9. In such a case, the conveyor 325 moves the palette 265 along the first horizontal lane 261 in a predetermined direction and, subsequently, moves the palette 265 in the direction opposite to the predetermined direction. Thereafter, the conveyor 325 turns the palette 265 around toward the second horizontal lane 263 and moves the palette 265 along the second horizontal lane 263 in the predetermined direction and, subsequently, moves the palette 265 in the direction opposite to the predetermined direction. Thereafter, the conveyor 325 turns the palette 265 around toward the first horizontal lane 261. The conveyor 325 repeatedly performs the above-described operations. After the conveyor 325 moves the palette 265 along the first horizontal lane 261 in the predetermined direction and before the conveyor 325 moves the palette 265 in the direction opposite to the predetermined direction, the conveyor 325 carries in the palette 265 from 332 into the work area 330 as indicated by the arrow X and, thereafter, carries out the palette 265 from the work area 330 into the clean area 332 in a direction opposite to the direction of the arrow X. Note that as a modification that provides an inlet and outlet that serves as both an inlet and an outlet other than the above-described modification, the above-described modification can be applied to the clean work device 10 or the clean work device 110, for example.

The present application claims priority from Japanese Patent Application No. 2013-222187 filed on Oct. 25, 2013, the entire contents of which are incorporated herein by reference.

INDUSTRIAL APPLICABILITY

The present invention is applicable to a field of for example, regenerative medicine and pharmaceutical industry.

REFERENCE SIGNS LIST

Conveyor group 20, carry-in conveyor 21, upstream conveyor 23, conveyor 25 in work area, placement surface 25S, downstream conveyor 27, carry-out conveyor 29, work area 30, inlet 30a (first inlet, and outlet), outlet 30b (second inlet and outlet), clean area 32, inlet 32a, outlet 32b, wall 33, buffering area 34, inlet 34a, outlet 34b, well 35, buffering area 36, inlet 36a, outlet 36b, wall 37, cleaning device 40, cleaning liquid processing chamber 42, ultraviolet processing chamber 44, work area air curtain 50, air outlet port 50a, air suction port 50b, clean area air curtains 52 and 54, air outlet ports 52a and 54a, air suction ports 52b and 54b, rollers 60 and 62, upper horizontal lane 61, lower horizontal lane 63, belts 64, 64a, and 64b, palette 65, pick-up hole 66, waste hole 68, tip case 70, cover 72, set hole 74, waste case 82, cover 82, waste bole 84, robot arm 90, liquid supply and discharge device 92, clean work device 110, conveyor 125, placement surface 125S, cleaning device 140, cleaning liquid processing chamber 142, ultraviolet processing chamber 144, clean work device 210, conveyor 225, placement surface 225S, buffering area 234, cleaning device 240, cleaning liquid processing chamber 242, ultraviolet processing chamber 244, inner peripheral rail 260, first horizontal lane 261, outer peripheral rail 262, second horizontal lane 263, palette 265, clean work device 310, conveyor 325, work area 330, inlet and outlet 330c, area 332, air curtain 350, vessel V, tip T, cells C, conveyance path P.

The invention claimed is:

1. A clean work device for use in a predetermined work sequentially performed on different objects, comprising:
   a work area disposed in a conveyance path of the object, the work area having an inlet and an outlet in the conveyance path, a downflow air curtain being provided at least at the inlet and the outlet, the downflow air curtain blowing out of an air outlet port and being sucked by an air suction port that faces the air outlet port;
   a conveyor configured to repeatedly perform an operation that moves a placement surface on which the object is placed from the inlet side of the work area into the work area and, thereafter, moves the placement surface from an outlet side of the work area to the outside of the work area and, subsequently, moves back the placement surface to the inlet side again;
   a cleaning device comprising cleaning chambers configured to clean the placement surface during a period of time from when the conveyor moves the placement surface to the outside of the work area and through the cleaning chambers until the conveyor moves back the placement surface to the inlet side of the work area;
   a clean area that includes the work area, the clean area extending upstream and downstream of the work area; and
   buffering areas provided on an upstream side and a downstream side of the clean area.

2. The clean work device according to claim 1, wherein the work area has the inlet on the upstream side of the conveyance path and the outlet on the downstream side of the conveyance path.

3. The clean work device according to claim 1, wherein the work area has the inlet that is the same as the outlet.

4. The clean work device according to claim 1, wherein the entire periphery of the work area is surrounded by the air curtain.

5. The clean work device according to claim 1, wherein the conveyor repeatedly performs an operation that moves the placement surface along an upper horizontal lane including the work area in a predetermined direction, turns over and leads the placement surface to a lower horizontal lane that faces the upper horizontal lane, moves the placement surface along the lower horizontal lane in a direction opposite to the predetermined direction, and turns over and leads the placement surface to the upper horizontal lane.

6. The clean work device according to claim 1, further comprising:
   an upstream-side conveyor disposed on the upstream side of and adjacent to the conveyor with the air curtain provided for the inlet of the work area therebetween.

7. The clean work device according to claim 1, further comprising:
   a downstream-side conveyor disposed on the downstream side of and adjacent to the conveyor with the air curtain provided for the outlet of the work area therebetween.

8. The clean work device according to claim 1, wherein the conveyor repeatedly performs an operation that moves the placement surface along a first horizontal lane including the work area in a predetermined direction, turns the placement surface around toward a second horizontal lane that is in the same plane as the first horizontal lane, moves the placement surface along the second horizontal lane in a direction opposite to the predetermined direction, and turns the placement surface around toward the first horizontal lane.

9. The clean work device according to claim 1, wherein the conveyor is a conveyor using a belt, and
   wherein the belt has an air passage in a portion thereof that is located between the air outlet port and the air suction port that face each other when the belt is positioned at a predetermined work position.

10. The clean work device according to claim 1, wherein downflow air that is weaker than the air curtain flows in the work area.

* * * * *